(12) United States Patent
Burg

(10) Patent No.: US 9,474,802 B2
(45) Date of Patent: Oct. 25, 2016

(54) COMPOSITIONS AND METHODS TO REDUCE HANGOVER AND REDUCE BLOOD ALCOHOL LEVELS AFTER ALCOHOL CONSUMPTION

(76) Inventor: Jonathan Burg, Albuquerque, NM (US)

( * ) Notice: Subject to any disclaimer, the term of this patent is extended or adjusted under 35 U.S.C. 154(b) by 810 days.

(21) Appl. No.: 13/882,386

(22) PCT Filed: Oct. 28, 2011

(86) PCT No.: PCT/US2011/058379
§ 371 (c)(1),
(2), (4) Date: Apr. 29, 2013

(87) PCT Pub. No.: WO2012/058589
PCT Pub. Date: May 3, 2012

(65) Prior Publication Data
US 2013/0224319 A1    Aug. 29, 2013

Related U.S. Application Data

(60) Provisional application No. 61/407,722, filed on Oct. 28, 2010.

(51) Int. Cl.
| | | |
|---|---|---|
| A01N 65/00 | (2009.01) |
| A61K 45/06 | (2006.01) |
| A61K 31/198 | (2006.01) |
| A61K 31/375 | (2006.01) |
| A61K 31/4415 | (2006.01) |
| A61K 31/51 | (2006.01) |
| A61K 31/7004 | (2006.01) |
| A61K 36/28 | (2006.01) |
| A61K 36/33 | (2006.01) |
| A61K 36/48 | (2006.01) |
| A61K 36/488 | (2006.01) |
| A61K 36/752 | (2006.01) |
| A61K 36/76 | (2006.01) |

(52) U.S. Cl.
CPC ............. *A61K 45/06* (2013.01); *A61K 31/198* (2013.01); *A61K 31/375* (2013.01); *A61K 31/4415* (2013.01); *A61K 31/51* (2013.01); *A61K 31/7004* (2013.01); *A61K 36/28* (2013.01); *A61K 36/33* (2013.01); *A61K 36/48* (2013.01); *A61K 36/488* (2013.01); *A61K 36/752* (2013.01); *A61K 36/76* (2013.01)

(58) Field of Classification Search
CPC ...................................................... A61K 36/00
USPC ........................................................ 424/725
See application file for complete search history.

(56) References Cited

U.S. PATENT DOCUMENTS

| | | |
|---|---|---|
| 6,221,358 B1 | 4/2001 | Na et al. |
| 6,967,031 B1 | 11/2005 | Oslick et al. |
| 7,449,448 B2 | 11/2008 | McGregor |
| 2006/0112584 A1 | 6/2006 | Jones |
| 2007/0213400 A1 | 9/2007 | Okubo et al. |
| 2008/0075710 A1 | 3/2008 | Cornett et al. |
| 2008/0286392 A1 | 11/2008 | Takagaki et al. |
| 2010/0209557 A1 | 8/2010 | O'Connor et al. |

OTHER PUBLICATIONS

International search report for corresponding PCT application PCT/US2011/058379, mailed Mar. 2, 2012.

Primary Examiner — Michael Meller
(74) Attorney, Agent, or Firm — Wood, Phillips, Katz, Clark & Mortimer

(57) ABSTRACT

Compositions and methods for preventing and/or reducing hangover, when consumed before, after or during drinking alcohol. Compositions of the inventions include fructose powder, prickly pear extract, N-acetyl cysteine; kudzu; lemon balm; Vitamin C; nopal; white willow bark extract; milk thistle; Vitamin B1; Vitamin B6; lemon juice; acacia fiber; and other ingredients.

1 Claim, 2 Drawing Sheets

COMPOSITIONS AND METHODS TO REDUCE HANGOVER AND REDUCE BLOOD ALCOHOL LEVELS AFTER ALCOHOL CONSUMPTION

BACKGROUND OF THE INVENTION

Human beings have been enjoying fermented alcoholic beverages for millennia and have also been suffering the morning after effects (such as hangover) likely for just as long.

One of the major reasons for alcohol consumption is alcohol's effect on the central nervous system. The clinical effects are well characterized and range from mild euphoria to coma and death. A common side effect of excessive consumption is hangover, a symptom complex which may include headache, nausea, vomiting, thirst, dry mouth, tremors, dizziness, fatigue, muscle cramps, fuzzy cognition, poor visual-spatial coordination, pain, hallucinations, shaking and sweating. Hangover results in decreased productivity of the workforce, estimated to represent losses of $148 billion yearly in the US alone.

It would be beneficial to be able to reduce alcohol's effects on the central nervous system and to be able to reduce and/or prevent hangover. Thus, there is a need for a product which is effective at lowering alcohol level and preventing hangover following alcohol consumption.

BRIEF SUMMARY OF THE INVENTION

The compositions of the present invention are able to effectively and significantly reduce and/or eliminate hangover symptoms and to reduce blood alcohol levels as measured by a breathalyzer or another device when consumed prior to imbibing alcohol.

In one embodiment, the invention provides a liquid composition for preventing and/or reducing a hangover in a subject in need thereof comprising:
   a) from about 0.3 g/ml to about 0.5 g/ml of fructose powder;
   b) from about 10% to about 15% of prickly pear extract;
   c) from about 3 mg/ml to about 5 mg/ml of N-acetyl cysteine;
   d) from about 1 mg/ml to about 2 mg/ml of kudzu;
   e) from about 0.7 mg/ml to about 1.5 mg/ml of lemon balm;
   f) from about 0.7 mg/ml to about 1.5 mg/ml of Vitamin C;
   g) from about 0.5 mg/ml to about 1.3 mg/ml of nopal;
   h) from about 0.5 mg/ml to about 1.3 mg/ml of white willow bark extract;
   i) from about 0.4 mg/ml to about 1.2 mg/ml of milk thistle;
   j) from about 0.2 mg/ml to about 0.6 mg/ml of Vitamin B1;
   k) from about 0.2 mg/ml to about 0.6 mg/ml of Vitamin B6;
   l) from about 5% to about 10% of lemon juice;
   m) from about 0.2 mg/ml to about 0.6 mg/mi of acacia fiber;
   n) optionally, natural and artificial flavors and colors; and
   o) the balance of filtered water.

In a preferred embodiment, the composition of the invention has the total volume of about 240 ml and comprises:
   a) about 100 g of fructose powder;
   b) about 30 ml of prickly pear extract;
   c) about 1000 mg of N-acetyl cysteine;
   d) about 400 mg of kudzu;
   e) about 250 mg of lemon balm;
   f) about 250 mg of Vitamin C;
   g) about 200 mg of nopal;
   h) about 200 mg of white willow bark extract;
   h) about 175 mg of milk thistle;
   i) about 100 mg of Vitamin B1;
   j) about 100 mg of Vitamin B6;
   k) about 20 ml of lemon juice;
   l) about 100 mg of acacia fiber;
   m) optionally, natural and artificial flavors and colors; and
   n) the balance of filtered water.

The invention also provides a method of reducing and/or preventing hangover in a patient in need thereof comprising administering to said patient the compositions of the inventions.

The methods and compositions of the invention may also be used to treat, reduce and/or alleviate Asian flush reaction (also known as Oriental Flushing Syndrome, Asian Flush, Asian Glow, etc) or other conditions associated with an accumulation of acetaldehyde. The methods and compositions of the invention may also be used to treat, reduce, and/or alleviate any other side effects of drinking alcohol, including but not limited to redness of various bodily parts, such as face, flushes, blotches, migraines (including but not limited migraines caused by tyramine present in red wine), headaches, and any other side effects of alcohol consumption.

DETAILED DESCRIPTION OF THE INVENTION

Figure 1:
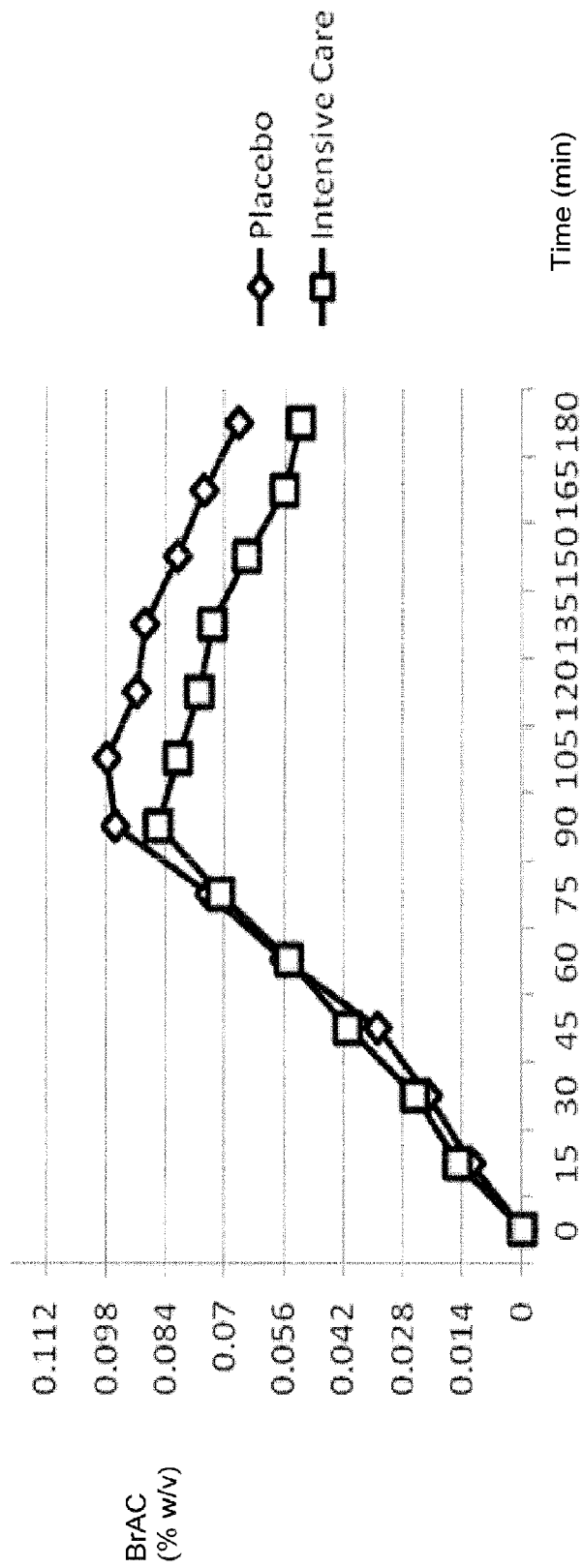
FIG. 1 is a chart describing the results of the effects of consuming the inventive composition following ingestion of alcohol.

The present invention provides compositions and methods which effectively and significantly reduce and/or eliminate hangover symptoms and to reduce blood alcohol levels as measured by a breathalyzer or another device.

In one embodiment, the invention provides a liquid composition for preventing and/or reducing a hangover and reducing blood alcohol levels in a subject in need thereof comprising:
   a) from about 0.3 g/ml to about 0.5 g/ml of fructose powder;
   b) from about 10% to about 15% of prickly pear extract;
   c) from about 3 mg/ml to about 5 mg/ml of N-acetyl cysteine;
   d) from about 1 mg/ml to about 2 mg/ml of kudzu;
   e) from about 0.7 mg/ml to about 1.5 mg/ml of lemon balm;
   f) from about 0.7 mg/ml to about 1.5 mg/ml of Vitamin C;
   g) from about 0.5 mg/ml to about 1.3 mg/ml of nopal;
   h) from about 0.5 mg/ml to about 1.3 mg/ml of white willow bark extract;
   i) from about 0.4 mg/ml to about 1.2 mg/ml of milk thistle;
   j) from about 0.2 mg/ml to about 0.6 mg/ml of Vitamin B1;
   k) from about 0.2 mg/ml to about 0.6 mg/ml of Vitamin B6;
   l) from about 5% to about 10% of lemon juice;

m) from about 0.2 mg/ml to about 0.6 mg/ml of acacia fiber;

n) optionally, natural and artificial flavors and colors; and o) the balance of filtered water.

In a preferred embodiment, the composition of the invention has the total volume of about 240 ml and comprises:

a) about 100 g of fructose powder;

b) about 30 ml of prickly pear extract;

c) about 1000 mg of N-acetyl cysteine;

d) about 400 mg of kudzu;

e) about 250 mg of lemon balm;

f) about 250 mg of Vitamin C;

g) about 200 mg of nopal;

h) about 200 mg of white willow bark extract;

h) about 175 mg of milk thistle;

i) about 100 mg of Vitamin B1;

j) about 100 mg of Vitamin B6;

k) about 20 ml of lemon juice;

l) about 100 mg of acacia fiber;

m) optionally, natural and artificial flavors and colors; and n) the balance of filtered water.

The composition provided in the preferred embodiment may be referred to as "Intensive Care" composition for the purposes of the present invention.

Although in some embodiments, the provided compositions may be combined with other ingredients, the compositions of the invention do not require any other ingredients to reduce and/or preventing hangover or to lower the blood alcohol level.

Liquid compositions of the invention may be provided in various forms, including but not limited to ready-to-use solutions, concentrates that are later to be diluted by a consumer, additives, and other forms. The compositions may also be provided as powders which are released into a solution by a consumer; smoothies, etc.

Accordingly, in one embodiment, the invention provides a kit comprising: a) a dried or freeze-dried powder comprising from about 1000 gm fructose powder, about 1000 mg N-acetyl cysteine, about 400 mg kudzu, about 250 mg lemon balm, about 250 mg vitamin C, about 200 mg nopal, about 200 mg white willow bark extract (*Salix Alba*), about 175 mg milk thistle, about 100 mg vitamin B1, about 100 mg vitamin B6 and about 100 mg acacia fiber, and b) a liquid vehicle comprising about 30 ml prickly pear extract, about 20 ml of lemon juice, and about 160-180 ml filtered water so that the total volume of the final solution produced by combining the powder with the liquid vehicle is about 240 ml. Either the powder or the liquid vehicle may also include natural and artificial flavors and colors.

In some embodiments, some ingredients of the powder may be present in the liquid vehicle, and vice versa, as long as the final solution contains the ingredients in the proportions as indicated above. In other words, it is not critical which ingredients are provided in the powder form before the final solution is prepared; the key is the proportion of the ingredients in the final solution. This is because a key discovery of the invention is the specific combination of the ingredients at the specified proportions. It is believed that combining these ingredients at the specified proportions provides a synergistic effect which allows to significantly reduce and/or eliminate hangover symptoms and/or to reduce blood alcohol levels upon consumption of the compositions of the invention.

The invention also provides a method of reducing and/or preventing hangover and reducing blood alcohol levels in a patient in need thereof comprising administering to said patient the compositions of the inventions. It is best to consume the provided compositions as soon as possible after consumption of alcoholic beverages.

The methods and compositions of the invention may also be used to treat, reduce and/or alleviate Asian flush reaction (also known as Oriental Flushing Syndrome, Asian Flush, Asian Glow, etc) or other conditions associated with an accumulation of acetaldehyde. The methods and compositions of the invention may also be used to treat, reduce, and/or alleviate any other side effects of drinking alcohol, including but not limited to redness of various bodily parts, such as face, flushes, blotches, migraines (including but not limited migraines caused by tyramine present in red wine), headaches, and any other side effects of alcohol consumption.

In other embodiments, the compositions of the present invention may be consumed before alcohol consumption to reduce and/or prevent hangover and reduce blood alcohol levels.

In some embodiments, the compositions of the present invention may be consumed during alcohol consumption.

The compositions of the inventions may be stored and delivered using any delivery vehicles, including but not limited to bottles, caps, and any other suitable containers (including Blast-Cap®, Button-Blast®, Bottle-Blast®, and others). In some embodiments, the powder and the liquid components of the composition are stored in one device (such as a Blast-Cap®), while in other embodiments, the powder and the liquid components of the composition are stored in separate containers.

The present invention is more particularly described in the following non-limiting examples that are intended as illustrative only, since many modifications and variations therein will be apparent to those skilled in the art.

EXAMPLE 1

Alcohol Intoxication, Hangover and Breathalyzed Alcohol Level (BrAC) Reduction Study Purpose The purpose of this study was to determine the "alcohol decreasing" capabilities of an inventive composition when the inventive composition is consumed following ingestion of alcohol Design Five (5) subjects were chosen: 2 women (ages 24 and 25) and 3 men (ages 26, 25 and 28). Each subject served as his or her own control in terms of the response to alcohol challenge. Therefore, even the small number of subjects could result in statistically significant results.

Methods

First, a baseline alcohol metabolism for each subject was determined utilizing Jack Daniels bourbon (80 proof, 40%). To do that, each subject consumed one 1.5 oz serving ("a shot"), every 15 minutes for a total of 6 shots (9 oz). Directly prior to each "shot", a breathalyzed alcohol level (BrAC) was obtained.

One week later, the same method was repeated, except the "Intensive Care" composition was consumed 15 minutes following the last "shot" (shot #6).

Results

Table 1 below contains average BrAc levels (percent weight/volume) for the five subjects at various time points during the experiment.

TABLE 1

| Time points (min) | Placebo | Intensive Care |
| --- | --- | --- |
| 0 | 0 | 0 |
| 15 | 0.012 | 0.015 |
| 30 | 0.022 | 0.025 |
| 45 | 0.034 | 0.041 |
| 60 | 0.056 | 0.055 |
| 75 | 0.074 | 0.071 |
| 90 ("Intensive Care" composition consumed) | 0.096 | 0.086 |
| 105 | 0.098 | 0.081 |
| 120 | 0.091 | 0.076 |
| 135 | 0.089 | 0.073 |
| 150 | 0.081 | 0.065 |
| 165 | 0.075 | 0.056 |
| 180 | 0.067 | 0.052 |

FIG. 1 demonstrates the results of this experiment.

As Table 1 and FIG. 1 show, consuming the inventive composition resulted in a moderate reduction in BrAC values after alcohol consumption in each subject compared to controls. The reduction was as follows:

18% in the first 15 minutes (following the last shot of 6 shots);

16% 30 minutes after ingestion;

18% 45 minutes after ingestion;

21% 60 minutes after ingestion;

25% 75 minutes after ingestion; and finally

21% 90 minutes after ingestion.

Further, the subjects reported a markedly reduced subjective sense of inebriation compared to controls.

Objectively, 15 minutes after consumption of "Intensive Care" there was a significant difference from controls with the non-quantifiable testing of intoxication. There were no episodes of nausea, vomiting or diarrhea or any other side effects noted after consuming the inventive composition. Also, no hangover symptoms were experienced when the subjects awoke the next morning (7-9 hours later). In contrast, significant hangover symptoms were described in the control group.

EXAMPLE 2

Alcohol Intoxication, Hangover and Breathalyzed Alcohol Level (BrAC) Blocking with Pre-Treatment Study Purpose The purpose of this study was to determine the "alcohol blocking" capabilities of the inventive composition when consumed prior to ingestion of alcohol.

Design

Four (4) subjects were chosen: 1 woman aged 21 and 3 men aged 22, 25 and 28. Each subject served as his or her own control in terms of the response to the alcohol challenge. Therefore, even the small number of subjects could result in statistically significant results.

Methods

First, a baseline alcohol metabolism was determined for each subject utilizing Kettle One vodka (80 proof, 40%). Each subject consumed 2.25 oz (one and a half "shots") every 15 minutes. Directly prior to each "shot", a breathalyzed alcohol level (BrAC) was obtained.

One week later, the same method was repeated, except the "Intensive Care" composition was consumed 15 minutes before the first "shot" (shot #1).

Results

Table 2 below contains average BrAc levels (percent weight/volume) for the four subjects at various time points during the experiment.

TABLE 2

| Time points (min) | Placebo | Intensive Care |
| --- | --- | --- |
| −15("Intensive Care" composition consumed) | 0 | 0 |
| 0 | 0 | 0 |
| 15 | 0.013 | 0 |
| 30 | 0.028 | 0.003 |
| 45 | 0.046 | 0.019 |
| 60 | 0.064 | 0.028 |

Figure 2:
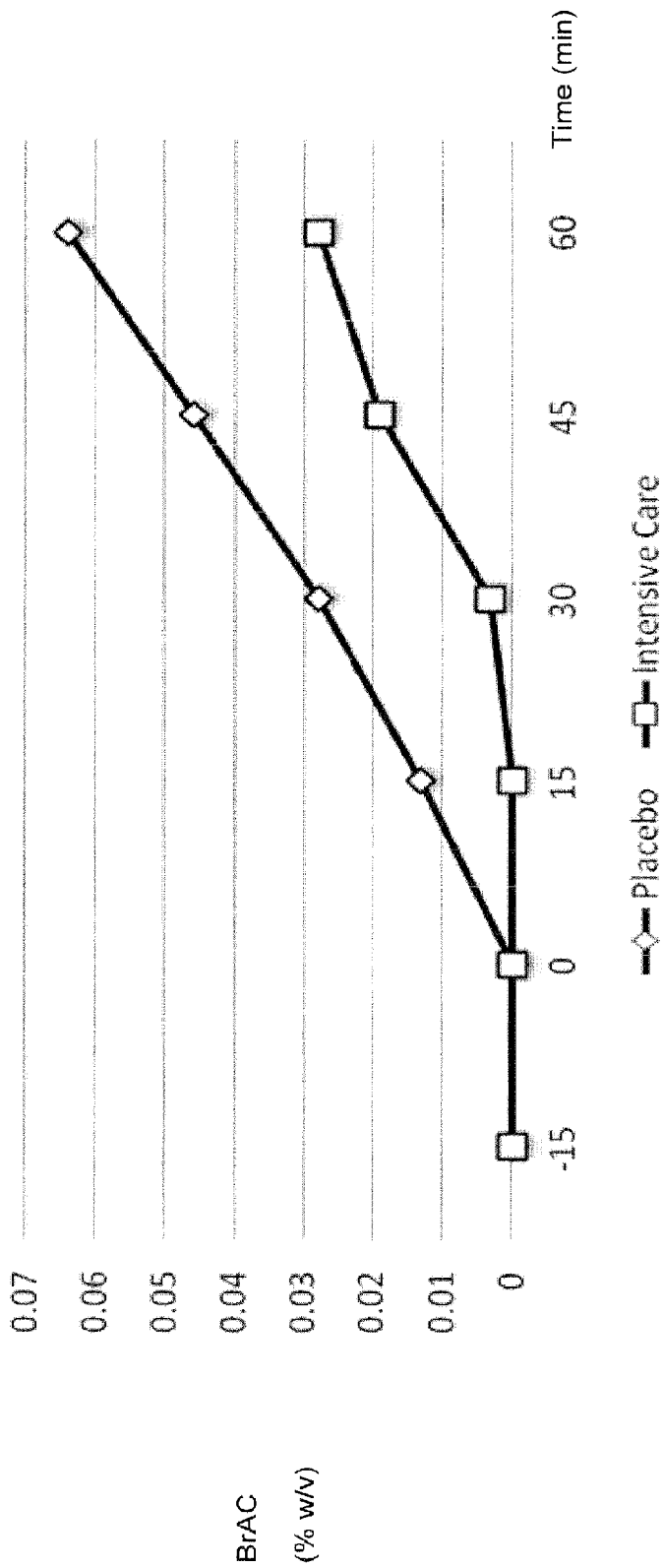
FIG. 2 is a chart describing the results of the effects of consuming the inventive composition before ingestion of alcohol.

FIG. 2 demonstrates the results of this experiment.

As Table 2 and FIG. 2 show, consuming the inventive composition before drinking the first shot resulted in a marked reduction in BrAC values after alcohol consumption in each subject compared to controls.

The reduction was as follows:

15 minutes after the first shot: 100%;

30 minutes after the first shot: 89%;

45 minutes after the first shot: 58%; and 60 minutes after the first shot: 56%.

The average reduction compared to the controls in BrAC levels after the last shot was 56%.

Further, nobody in the treated group reported any subjective symptoms of intoxication after the last "shot," whereas everyone in the control group admitted feeling intoxicated. In addition, nobody in the pre-treatment group demonstrated any objective signs of intoxication, whereas the non-treated group was very obviously intoxicated on casual observation and non-quantifiable balance and cognitive testing after the last shot. Further, there was no hangover experienced in the morning in the pre-treatment group, and all subjects woke up energized. In contrast, all non-treatment subjects reported hangover symptoms.

What is claimed is:

1. A method of reducing a hangover and reducing alcohol levels in a human in need thereof comprising administering to said human in need thereof a composition comprising:
   a) from about 0.3 g/ml to about 0.5 g/ml of fructose powder;
   b) from about 10% to about 15% of prickly pear extract;
   c) from about 3 mg/ml to about 5 mg/ml of N-acetyl cysteine;
   d) from about 1 mg/ml to about 2 mg/ml of kudzu;
   e) from about 0.7 mg/ml to about 1.5 mg/ml of lemon balm;
   f) from about 0.7 mg/ml to about 1.5 mg/ml of Vitamin C;
   g) from about 0.5 mg/ml to about 1.3 mg/ml of nopal;
   h) from about 0.5 mg/ml to about 1.3 mg/ml of white willow bark extract;
   i) from about 0.4 mg/ml to about 1.2 mg/ml of milk thistle;
   j) from about 0.2 mg/ml to about 0.6 mg/ml of Vitamin B1;
   k) from about 0.2 mg/ml to about 0.6 mg/ml of Vitamin B6;

l) from about 5% to about 10% of lemon juice;
m) from about 0.2 mg/ml to about 0.6 mg/ml of acacia fiber; and
n) the balance of the composition being filtered water, wherein after said composition is administered to said human in need thereof the hangover and the alcohol levels in the human are reduced.

\* \* \* \* \*